(12) United States Patent
Chiodo et al.

(10) Patent No.: US 9,340,536 B2
(45) Date of Patent: May 17, 2016

(54) MULTICOMPONENT CRYSTALS COMPRISING DASATINIB AND SELECTED CO-CRYSTAL FORMERS

(71) Applicant: BASF SE, Ludwigshafen (DE)

(72) Inventors: Tiziana Chiodo, Mannheim (DE); Andreas Hafner, Gelterkinden (CH); Tobias Hintermann, Therwil (CH); Beate Salvador, Ellerstadt (DE); Martin Szelagiewicz, Basel (CH); Fritz Blatter, Reinach (CH); Bernd Siebenhaar, Kandern-Wollbach (DE); Marcus Vossen, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/406,339

(22) PCT Filed: Jun. 13, 2013

(86) PCT No.: PCT/IB2013/054832
§ 371 (c)(1),
(2) Date: Dec. 8, 2014

(87) PCT Pub. No.: WO2013/186726
PCT Pub. Date: Dec. 19, 2013

(65) Prior Publication Data
US 2015/0133463 A1    May 14, 2015

Related U.S. Application Data

(60) Provisional application No. 61/659,997, filed on Jun. 15, 2012.

(30) Foreign Application Priority Data

Jun. 15, 2012    (EP) .................................... 12172172

(51) Int. Cl.
| | | |
|---|---|---|
| *C07D 417/12* | (2006.01) |
| *A61K 31/506* | (2006.01) |
| *C07C 35/12* | (2006.01) |
| *C07C 47/58* | (2006.01) |
| *C07C 65/03* | (2006.01) |
| *C07D 213/82* | (2006.01) |
| *C07D 309/40* | (2006.01) |

(52) U.S. Cl.
CPC ............ *C07D 417/12* (2013.01); *A61K 31/506* (2013.01); *C07C 35/12* (2013.01); *C07C 47/58* (2013.01); *C07C 65/03* (2013.01); *C07D 213/82* (2013.01); *C07D 309/40* (2013.01); *C07B 2200/13* (2013.01)

(58) Field of Classification Search
CPC .......................... C07D 417/12; A61K 31/506
USPC ..................... 544/295; 514/252.19
See application file for complete search history.

(56) References Cited

U.S. PATENT DOCUMENTS

| | | |
|---|---|---|
| 6,596,746 B1 | 7/2003 | Das et al. |
| 7,491,725 B2 | 2/2009 | Lajeunesse et al. |
| 7,696,203 B2 * | 4/2010 | Smith et al. ................ 514/232.5 |
| 7,973,045 B2 | 7/2011 | Simo et al. |
| 8,067,423 B2 | 11/2011 | Simo et al. |
| 8,716,305 B2 | 5/2014 | Hafner et al. |
| 8,796,481 B2 | 8/2014 | Berens et al. |
| 8,841,316 B2 | 9/2014 | Hafner et al. |
| 2004/0024208 A1 | 2/2004 | Das et al. |
| 2004/0073026 A1 | 4/2004 | Das et al. |
| 2004/0077875 A1 | 4/2004 | Das et al. |
| 2005/0261305 A1 | 11/2005 | Das et al. |
| 2005/0288303 A1 | 12/2005 | Barrish et al. |
| 2006/0004067 A1 | 1/2006 | Chen et al. |

(Continued)

FOREIGN PATENT DOCUMENTS

| | | |
|---|---|---|
| CN | 102030745 A | 4/2011 |
| EP | 2 308 833 A2 | 4/2011 |

(Continued)

OTHER PUBLICATIONS

U.S. Appl. No. 14/433,147, filed Apr. 2, 2015, Chiodo, et al.

(Continued)

*Primary Examiner* — Deepak Rao
(74) *Attorney, Agent, or Firm* — Oblon, McClelland, Maier & Neustadt, L.L.P.

(57) ABSTRACT

Provided are a multicomponent crystalline system (co-crystal), use thereof, as well as a process for obtaining the same. The said multicomponent crystalline system (co-crystal) comprises Dasatinib and a second compound selected from methylM-hydrobenzoate, nicotinamide, ethyl gallate, methyl gallate, propyl gallate, ethyl maltol, vanillin, menthol, or (1R,2S,5R)-(−)-menthol.

formula 1

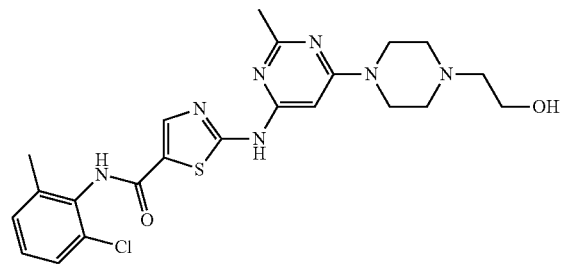

19 Claims, 7 Drawing Sheets

(56) References Cited

U.S. PATENT DOCUMENTS

| | | |
|---|---|---|
| 2006/0079563 A1 | 4/2006 | Das et al. |
| 2008/0306100 A1* | 12/2008 | Kompella et al. .............. 514/275 |
| 2009/0118297 A1 | 5/2009 | Simo et al. |
| 2009/0306086 A1* | 12/2009 | Ibrahim et al. ................. 514/249 |
| 2010/0063107 A1* | 3/2010 | Smith et al. .................... 514/341 |
| 2010/0256158 A1* | 10/2010 | Simo et al. ................ 514/252.19 |
| 2013/0237553 A1 | 9/2013 | Hafner et al. |
| 2014/0155371 A1 | 6/2014 | Hafner et al. |

FOREIGN PATENT DOCUMENTS

| | | |
|---|---|---|
| WO | WO 00/62778 A1 | 10/2000 |
| WO | WO 2005/077945 A2 | 8/2005 |
| WO | WO 2007/035874 A1 | 3/2007 |
| WO | WO 2009/053854 A2 | 4/2009 |
| WO | WO 2010/062715 A2 | 6/2010 |
| WO | WO 2010/067374 A2 | 6/2010 |
| WO | WO 2010/081443 A2 | 7/2010 |
| WO | WO 2012/014149 A1 | 2/2012 |
| WO | WO 2012/069394 A1 | 5/2012 |
| WO | WO 2012/143308 A1 | 10/2012 |
| WO | WO 2013/014604 A1 | 1/2013 |
| WO | WO 2013/084130 A1 | 6/2013 |
| WO | WO 2013/098370 A1 | 7/2013 |
| WO | WO 2013/143927 A1 | 10/2013 |
| WO | WO 2013/174693 A1 | 11/2013 |
| WO | WO 2013/174694 A1 | 11/2013 |
| WO | WO 2013/186726 A2 | 12/2013 |

OTHER PUBLICATIONS

U.S. Appl. No. 14/360,799, filed May 27, 2014, Hafner, et al.
U.S. Appl. No. 14/388,462, filed Sep. 26, 2014, Chiodo, et al.
U.S. Appl. No. 14/406,264, filed Dec. 8, 2014, Chiodo, et al.
International Search Report issued Dec. 5, 2013 in PCT/IB2013/054832.
European Search Report issued May 2, 2013 in Patent Application No. EP 12 17 2172.
Martin Viertelhaus, et al., "Piracetam Co-Crystals with OH-Group Functionalized Carboxylic Acids", Crystal Growth & Design, 2009 American Chemical Society, vol. 9, No. 5, (2009), pp. 2220-2228.
U.S. Appl. No. 14/415,875, filed Jan. 20, 2015, Hafner, et al.

* cited by examiner

MULTICOMPONENT CRYSTALS COMPRISING DASATINIB AND SELECTED CO-CRYSTAL FORMERS

Dasatinib which is also known as BMS-354825 was disclosed in WO Patent Publication No. 00/62778 and in U.S. Pat. No. 6,596,746. Dasatinib, chemically N-(2-chloro-6-methylphenyl)-2-[[6-[4-(2-hydroxyethyl)-1-piperazinyl]-2-methyl-4-pyrimidinyl]amino]-5-thiazolecarboxamide, is represented by the following structure:

formula 1

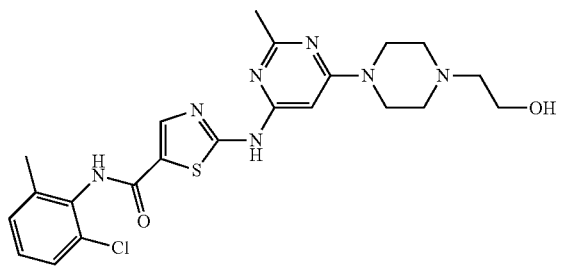

Dasatinib is a drug produced by Bristol-Myers Squibb and sold under the trade name Sprycel® (which contains Dasatinib monohydrate as the active ingredient). Dasatinib is an oral dual BCR/ABL and Src family tyrosine kinase inhibitor approved for use in patients with chronic myelogenous leukemia (CML) after imatinib treatment and Philadelphia chromosome-positive acute lymphoblastic leukemia (Ph+ ALL).

The present invention refers to a multicomponent crystalline system (co-crystal) comprising a compound of formula 1 (INN: Dasatinib)

formula 1

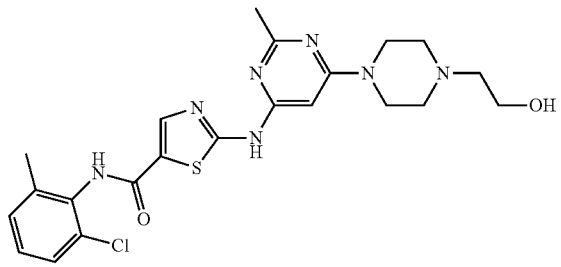

and a second compound selected from methyl-4-hydroxybenzoate, or nicotinamide, or ethyl gallate, or methyl gallate, or propyl gallate, or ethyl maltol or vanillin, or menthol, or (1R,2S,5R)-(−)-menthol.

Dastinib is an achiral compound, since it does not contain a chiral center. The second compound is also referred to as co-crystal former.

In the context of the present invention methyl-4-hydroxybenzoate, nicotinamide, ethyl gallate, methyl gallate, propyl gallate, ethyl maltol vanillin, (1R,2S,5R)-(−)-menthol and menthol are co-crystal formers being solid at ambient temperature (in contrast to a solvate in which the second component would be liquid at ambient temperature). Thus, the multicomponent crystalline system of the present invention can be regarded as being a co-crystal.

Herein, the term multicomponent crystal or multicomponent crystalline phase or crystalline composition is synonymous to the term co-crystal as defined in Viertelhaus et. al., Cryst. Growth & Design, 2009, 9 (5), 2220-2228. However, the co-crystals of this invention can exist in variable molar ratios of Dasatinib to co-crystal former.

In the context of the present invention, ambient temperature is room temperature, being preferably 20 to 30° C. and most preferably 20 to 25° C.

Preferably, in the context of the present invention menthol is preferably (1R,2S,5R)-(−)-menthol or its enantiomer (1S, 2R,5S)-(+)-menthol.

One embodiment of the invention is a multicomponent crystalline system of Dasatinib with methyl-4-hydroxybenzoate, or nicotinamide, or ethyl gallate, or methyl gallate, or propyl gallate, or ethyl maltol or vanillin, or menthol, or (1R,2S,5R)-(−)-menthol that is forming a single crystalline phase. The invention is further related to pharmaceutical preparations comprising said system. Furthermore, the invention also relates to processes for preparing said multicomponent system and/or crystalline phases. The invention also relates to compositions comprising said multicomponent system and/or crystalline phase and a pharmaceutically acceptable carrier, and to methods of using said multicomponent system or crystalline phase to treat a disease.

Dasatinib is known to exist in close to 60 solid-state forms: a monohydrate, four anhydrous and unsolvated forms which are described in U.S. Pat. No. 7,491,725B2, US2006/0004067A1, U.S. Pat. No. 7,973,045B2, and WO2010/067374, and therein referred to as forms N-6, T1H1-7, B, and I. Furthermore, an amorphous form and 52 solvates are known from WO2007/035874, US2006/0004067A, WO2009/053854A2, U.S. Pat. No. 8,067,423B, WO2010/062715, and CN102030745. In particular, patent application WO 2010/062715 includes the solvents isosorbide dimethyl ether, N,N'-dimethylethylene urea and N,N'-dimethyl-N,N'-propylene urea. Isosorbide dimethyl ether is used in cosmetic and pharmaceutical formulations.

Co-crystal formation with fructose and lactose (1:1 and 1:2 co-crystals) is mentioned in patent application WO 2010/081443 but no specific information is given neither concerning the formation, nor are there any characteristic data presented that would confirm their existence. All attempts to reproduce said co-crystals failed.

The discovery of new crystal forms of a pharmaceutically useful compound offers an opportunity to improve the performance profile of a pharmaceutical product. It widens the reservoir of materials a formulation scientist has available for designing a new dosage form of a drug with improved characteristics. One of the most important characteristics of an active pharmaceutical ingredient such as Dasatinib is the bioavailability which is often determined by the aqueous solubility.

A compound like Dasatinib, may give rise to a variety of crystalline forms having distinct crystal structures and physical characteristics like melting point, X-ray diffraction pattern, infrared spectrum, Raman spectrum, and solid state NMR spectrum. One crystalline form may give rise to thermal behavior different from that of another crystalline form. Thermal behavior can be measured in the laboratory by such techniques as capillary melting point, thermogravimetric analysis (TGA), and differential scanning calorimetry (DSC) as well as content of solvent in the crystalline form, which have been used to distinguish polymorphic forms.

Existing solid forms of Dasatinib still leave room for improvement of physical as well as biological characteristics, because the aqueous solubility of Dasatinib monohydrate is very poor. There exists a need for providing other solid forms, especially crystalline forms, N-(2-chloro-6-methylphenyl)-

2-[[6-[4-(2-hydroxyethyl)-1-piperazinyl]-2-methyl-4-pyrimidinyl]amino]-5-thiazolecarboxamide. Another object is to provide material to optimize manufacture, formulation, stability, and biological efficiency.

One reason is the highly complex polymorph landscape of said compound and the hereto related difficulties to produce a single and pure anhydrous crystalline form comprising Dasatinib that is essentially free of residual solvent.

SUMMARY OF THE INVENTION

The invention provides novel multicomponent crystalline systems (co-crystals) of Dasatinib comprising methyl-4-hydroxybenzoate, or nicotinamide, or ethyl gallate, or methyl gallate, or propyl gallate, or ethyl maltol, or menthol, or (1R,2S,5R)-(−)-menthol, or vanillin and, consequently, novel pharmaceutical formulations containing these co-crystals. The invention further provides processes for manufacture thereof and embodies methods of using said multicomponent system or crystalline phase to treat a disease.

The molar ratio of Dasatinib and the corresponding co-crystal former that is selected from the group consisting of methyl-4-hydroxybenzoate, nicotinamide, ethyl gallate, methyl gallate, propyl gallate, ethyl maltol, menthol, (1R,2S,5R)-(−)-menthol or vanillin is generally in the range from 7:1 to 1:1.

DETAILED DESCRIPTION OF THE INVENTION

The present invention is directed to a multicomponent crystalline system (co-crystal) comprising a compound of formula 1 (INN: Dasatinib)

formula 1

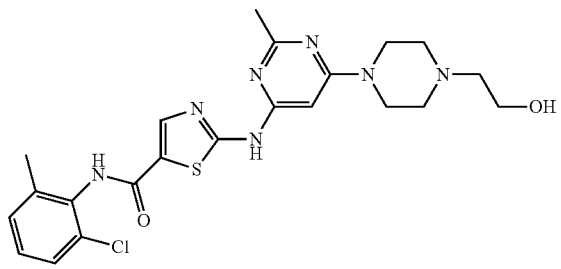

and a second compound selected from methyl-4-hydroxybenzoate, or nicotinamide, or ethyl gallate, or methyl gallate, or propyl gallate, or ethyl-maltol or vanillin, or menthol, or (1R,2S,5R)-(−)-menthol.

The second compound methyl-4-hydroxybenzoate, or nicotinamide, or ethyl gallate, or methyl gallate, or propyl gallate, or ethyl-maltol or vanillin, or menthol, or (1R,2S,5R)-(−)-menthol are also referred to as co-crystal former.

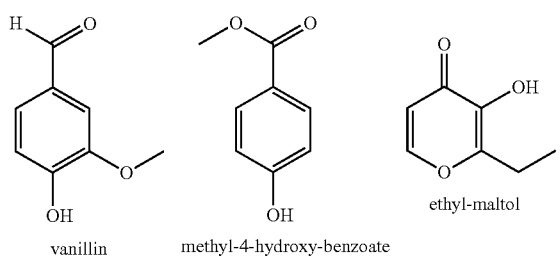

vanillin    methyl-4-hydroxy-benzoate    ethyl-maltol

-continued

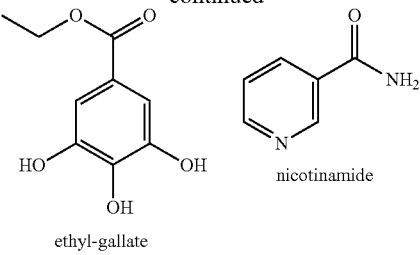

ethyl-gallate    nicotinamide

It has been the finding of the present invention that Dasatinib is able to form single crystalline phases (i.e. forming co-crystals) together with methyl-4-hydroxybenzoate, or nicotinamide, or ethyl gallate, or methyl gallate, or propyl gallate, or ethyl maltol, or menthol, or (1R,2S,5R)-(−)-menthol, or vanillin.

Preferably, the molar ratio of the compound of formula 1 and methyl-4-hydroxybenzoate, or nicotinamide, or ethyl gallate, or methyl gallate, or propyl gallate, or ethyl maltol, menthol, or (1R,2S,5R)-(−)-menthol, or vanillin is the range of from 7:1 to 1:1. More preferably the molar ratio of the compound of formula 1 to the co-crystal former is 4:1 to 2:1, and even more preferred ratio is 3.5:1 to 2.5:1. In a further preferred embodiment the molar ratio is 3:1.

The multicomponent crystalline system of the invention, thus, preferably consists essentially of Dasatinib (i.e. the compound of formula 1) and methyl-4-hydroxybenzoate, or nicotinamide, or ethyl gallate, or propyl gallate, or methyl gallate, or ethyl maltol, or menthol, or (1R,2S,5R)-(−)-menthol, or vanillin.

In a further preferred embodiment, the multicomponent crystalline system (co-crystal) is characterized in that the co-crystal former is methyl-4-hydroxybenzoate. This co-crystal exhibits a distinct PXRD pattern with at least one characteristic peak (expressed in 2θ±0.2° 2θ (CuKα radiation)) selected from the following peaks located at 6.0, 6.9, 12.0, 12.4, 13.2, 24.3; typically showing all of these peaks. A respective PXRD pattern is shown in FIG. 1.

In yet a further preferred embodiment, the multicomponent crystalline system (co-crystal) is characterized in that the co-crystal former is methyl-4-hydroxybenzoate. This co-crystal exhibits a distinct PXRD pattern with at least one characteristic peak (expressed in 2θ±0.2° 2θ (CuKα radiation)) selected from the following peaks located at 6.0, 6.9, 12.0, 12.4, 13.2, 13.8, 15.3, 16.8, 21.0, 24.3, 24.8, 26.7; typically showing all of these peaks. A respective PXRD pattern is shown in FIG. 1.

In a further preferred embodiment, the multicomponent crystalline system (co-crystal) is characterized in that the co-crystal former is nicotinamide. This co-crystal exhibits a distinct PXRD pattern with at least one characteristic peak (expressed in 2θ±0.2° 2θ (CuKα radiation)) selected from the following peaks located at 5.4, 5.9, 6.9, 12.4, 13.2, 24.4; typically showing all of these peaks. A respective PXRD pattern is shown in FIG. 2.

In a further preferred embodiment, the multicomponent crystalline system (co-crystal) is characterized in that the co-crystal former is nicotinamide. This co-crystal exhibits a distinct PXRD pattern with at least one characteristic peak (expressed in 2θ±0.2° 2θ (CuKα radiation)) selected from the following peaks located at 5.4, 5.9, 6.9, 11.8, 12.4, 13.2, 13.8, 15.1, 16.8, 17.7, 21.2, 24.4, 24.9; typically showing all of these peaks. A respective PXRD pattern is shown in FIG. 2.

In a further preferred embodiment, the multicomponent crystalline system (co-crystal) is characterized in that the co-crystal former is ethyl gallate. This co-crystal exhibits a distinct PXRD pattern with at least one characteristic peak (expressed in 2θ±0.2° 2θ (CuKα radiation)) selected from the following peaks located at 5.9, 6.9, 12.4, 13.2, 16.7, 21.1, 24.4; typically showing all of these peaks. A respective PXRD pattern is shown in FIG. 3.

In a further preferred embodiment, the multicomponent crystalline system (co-crystal) is characterized in that the co-crystal former is ethyl gallate. This co-crystal exhibits a distinct PXRD pattern with at least one characteristic peak (expressed in 2θ±0.2° 2θ (CuKα radiation)) selected from the following peaks located at 5.9, 6.9, 12.4, 13.2, 13.8, 16.7, 17.2, 21.1, 21.8, 24.4, 24.9, 27.8; typically showing all of these peaks. A respective PXRD pattern is shown in FIG. 3.

In a further preferred embodiment, the multicomponent crystalline system (co-crystal) is characterized in that the co-crystal former is ethyl maltol. This co-crystal exhibits a distinct PXRD pattern with at least one characteristic peak (expressed in 2θ±0.2° 2θ (CuKα radiation)) selected from the following peaks located at 5.9, 6.9, 11.8, 12.4, 13.2, 16.8; typically showing all of these peaks. A respective PXRD pattern is shown in FIG. 4.

In a further preferred embodiment, the multicomponent crystalline system (co-crystal) is characterized in that the co-crystal former is ethyl maltol. This co-crystal exhibits a distinct PXRD pattern with at least one characteristic peak (expressed in 2θ±0.2° 2θ (CuKα radiation)) selected from the following peaks located at 5.9, 6.9, 11.8, 12.4, 13.2, 13.8, 14.9, 16.8, 24.3, 24.9; typically showing all of these peaks. A respective PXRD pattern is shown in FIG. 4.

In a further preferred embodiment, the multicomponent crystalline system (co-crystal) is characterized in that the co-crystal former is vanillin. This co-crystal exhibits a distinct PXRD pattern with at least one characteristic peak (expressed in 2θ±0.2° 2θ (CuKα radiation)) selected from the following peaks located at 5.9, 6.9, 12.4, 13.2, 16.7, 24.4; typically showing all of these peaks. A PXRD pattern is shown in FIG. 5.

In a further preferred embodiment, the multicomponent crystalline system (co-crystal) is characterized in that the co-crystal former is vanillin. This co-crystal exhibits a distinct PXRD pattern with at least one characteristic peak (expressed in 2θ±0.2° 2θ (CuKα radiation)) selected from the following peaks located at 5.9, 6.9, 11.2, 12.4, 13.2, 13.8, 16.7, 17.2, 17.7, 24.1, 24.4, 24.9, 27.8; typically showing all of these peaks. A respective PXRD pattern is shown in FIG. 5.

In a further preferred embodiment, the multicomponent crystalline system (co-crystal) is characterized in that the co-crystal former is methyl gallate. This co-crystal exhibits a distinct PXRD pattern with at least one characteristic peak (expressed in 2θ±0.2° 2θ (CuKα radiation)) selected from the following peaks located at 6.0, 6.8, 12.0, 13.1, 15.5, 24.9; typically showing all of these peaks. A respective PXRD pattern is shown in FIG. 6.

In a further preferred embodiment, the multicomponent crystalline system (co-crystal) is characterized in that the co-crystal former is methyl gallate. This co-crystal exhibits a distinct PXRD pattern with at least one characteristic peak (expressed in 2θ±0.2° 2θ (CuKα radiation)) selected from the following peaks located at 6.0, 6.8, 12.0, 12.3, 13.1, 13.7, 15.5, 16.7, 18.0, 21.8, 24.3, 24.9; typically showing all of these peaks. A respective PXRD pattern is shown in FIG. 6.

In a further preferred embodiment, the multicomponent crystalline system (co-crystal) is characterized in that the co-crystal former is menthol and preferably (1R,2S,5R)-(−)-menthol. This co-crystal exhibits a distinct PXRD pattern with at least one characteristic peak (expressed in 2θ±0.2° 2θ (CuKα radiation)) selected from the following peaks located at 5.8, 6.8, 11.7, 13.7, 14.9; typically showing all of these peaks. A respective PXRD pattern is shown in FIG. 7.

In a further preferred embodiment, the multicomponent crystalline system (co-crystal) is characterized in that the co-crystal former is menthol and preferably (1R,2S,5R)-(−)-menthol. This co-crystal exhibits a distinct PXRD pattern with at least one characteristic peak (expressed in 2θ±0.2° 2θ (CuKα radiation)) selected from the following peaks located at 5.8, 6.8, 11.7, 12.3, 13.1, 13.7, 14.9, 16.5, 16.7, 17.6, 21.3, 23.9; typically showing all of these peaks. A respective PXRD pattern is shown in FIG. 7.

Dasatinib and methyl-4-hydroxybenzoate, or nicotinamide, or ethyl gallate, or methyl gallate, or propyl gallate, or ethyl maltol, or menthol, or (1R,2S,5R)-(−)-menthol, or vanillin are present in the same solid phase in amounts as indicated above, as a homogeneous solid phase, i.e. forming a co-crystal.

A preferred novel crystalline form generally exhibits a characteristic X-ray powder diffraction pattern.

The multicomponent crystalline system according to the present invention can be used in the treatment of chronic myelogenous leukemia (CML), preferably after imatinib treatment and/or Philadelphia chromosome-positive acute lymphoblastic leukemia (Ph+ALL).

Another object of the invention is a process for obtaining the crystalline composition comprising the steps of:
a) providing a compound of formula 1 (INN: Dasatinib)

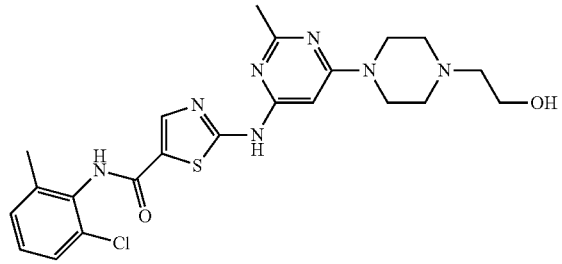

formula 1 in a suitable solvent or a mixture of solvents
b) adding methyl-4-hydroxybenzoate, or nicotinamide, or ethyl gallate, or methyl gallate, or propyl gallate, or menthol, or (1R,2S,5R)-(−)-menthol, or ethyl maltol or vanillin to the mixture of step a);
c) optionally concentrating the composition of step b);
d) crystallizing;
e) optionally evaporating to dryness or
equilibrating the obtained suspension of step d); and
f) isolating the obtained precipitate.

Preferably, the molar ratio of the compound of formula 1 in step a) and methyl-4-hydroxybenzoate, or nicotinamide, or ethyl gallate, or methyl gallate, or propyl gallate, or ethyl maltol, or menthol, or (1R,2S,5R)-(−)-menthol, or vanillin of step b) is in the range from 7:1 to 1:1.

Step b) usually comprises providing methyl-4-hydroxybenzoate, or nicotinamide, or ethyl gallate, or methyl gallate, or propyl gallate, or ethyl maltol, or menthol, or (1R,2S,5R)-(−)-menthol, or vanillin in solid form, or as a solution in methanol, or as a solution in an alcohol, a ketone, an acetate, of a mixture of solvents optionally containing water.

Preferably, the solvent used in step a) is a water miscible organic solvent such as an alcohol (e.g. methanol, ethanol, propanol, butanol) or an aprotic polar organic solvent such as DMSO, DMF, or NMP, or mixtures thereof.

Solutions or suspension according to steps a) and/or b) preferably are concentrated solutions. Preferably, the solvent is a water miscible organic solvent such as an alcohol (e.g. methanol, ethanol, propanol, butanol) and/or an aprotic polar organic solvent such as DMSO, DMF, or NMP, or a mixture thereof. Preferably the solvent used in step a) and/or step b) is methanol.

In a further preferred embodiment in step d) and/or e) seed crystals are added.

The concentration of Dasatinib in step a) may range from 0.1 to about 300 mg/ml of solvents, preferably from 5 to 200 mg/ml. The concentration of co-crystal former in step b) may range from 0.1 to about 300 mg/ml of solvents, preferably from 5 to 200 mg/ml.

The process is preferably carried out in the temperature range from 15-90° C. In a preferred process, steps a), b) and/or c) are carried out at a temperature in the range from 50-70° C. Preferably, the suspension is tempered and then cooled before step f) is carried out. In a preferred process, steps d) and/or e) are accompanied by seeding with crystals of the desired form of Dasatinib co-crystal (e.g. 1-10% by weight) at a temperature of about 20-60° C. In a further preferred process the solvent from the suspension of step e) is completely evaporated.

Optionally, the crystalline composition is isolated by filtering off the crystals and drying, e.g. in vacuum, an inert gas flow or both at ambient temperature, or elevated temperatures up to about 90° C.

The herein described multicomponent crystals show good kinetic and thermodynamic stability. Moreover, the multicomponent crystals (co-crystals) of the present invention are not prone to formation of solvates or hydrates.

The multicomponent crystalline system is generally obtained as a fine powder with typical particle size distributions with the median size between 1 and 50 µm, preferably between 1 to 10 µm. This particle size range ensures a fast dissolution profile, while retaining the favorable handling properties in the formulation process.

However, the most important advantage of the co-crystalline systems of this invention is the dramatically enhanced aqueous solubility. The aqueous solubility of the Dasatinib monohydrate was determined under the same conditions and according to the same protocol as the solubility of the multicomponent crystals (co-crystals).

Determination of the aqueous solubility of Dasatinib monohydrate (free base) resulted in an aqueous solubility of 0.36 microgram per milliliter (0.36 µg/mL). This value is consistent with the results from Fish et. al. in Journal of Pharmaceutical Innovation, 2009 (4) 165-173. However, the multicomponent crystals of the invention show aqueous solubilities that are at least factor of five greater then the solubility of the monohydrate form of Dasatinib (table 1). Roy et. al. in Cryst. Growth & Design, 2012 (12), 2122-2126 have estimated that the ratio of the equilibrium solubility of anhydrous Dasatinib free base to Dasatinib monohydrate free base is about 2.4; i.e.; anhydrous Dasatinib seems to be 2.4 times more soluble than the monohydrate. Therefore, the least soluble multicomponent crystal (co-crystal) of the invention is at least a factor of two more soluble than anhydrous Dasatinib (table 1).

TABLE 1

Aqueous solubility of Dasatinib monohydrate compared to the solubilities of the novel multicomponent crystalline systems (corrected to the effective solubility of the free drug substance).

| Solid-state form/co-crystal | Aqueous Solubility at 25° C. |
| --- | --- |
| Dasatinib free base monohydrate | 0.36 µg/mL |
| Dasatinib free base anhydrous form* | ~0.9 µg/mL |
| Dasatinib - methyl-4-hydroxybenzoate co-crystal | 2.1 µg/mL |
| Dasatinib - nicotinamide co-crystal | 11 µg/mL |
| Dasatinib - ethyl gallate co-crystal | 13 µg/mL |
| Dasatinib - ethyl maltol co-crystal | 9.4 µg/mL |
| Dasatinib - vanillin co-crystal | 11 µg/mL |
| Dasatinib - methyl gallate co-crystal | 42 µg/mL |
| Dasatinib - (1R,2S,5R)-(—)-menthol co-crystal | 2.3 µg/mL |

Measured after two hours equilibration time.
*Estimated value based on Roy et. al. in Cryst. Growth & Design, 2012 (12), 2122-2126.

A disadvantage of Dasatinib free base is the formation of more than 60 different crystalline forms which include a hydrate, several polymorphs and many solvated forms with essentially all organic solvents that are relevant for production process conditions in the pharmaceutical industry.

The co-crystals of the present invention may be used in pharmaceutical compositions in the same way as other forms of Dasatinib previously known. Additionally, the present co-crystalline systems may be employed as intermediates or starting materials to produce the pure active ingredient.

A further aspect of the present invention is a pharmaceutical composition comprising the multicomponent crystalline system of the present invention and optionally one or more pharmaceutically acceptable excipients. Moreover, the pharmaceutical composition may further comprise Imatinib as active ingredient.

The amount of the solid multicomponent crystalline system of the present invention (co-crystal) of N-(2-chloro-6-methylphenyl)-2-[[6-[4-(2-hydroxyethyl)-1-piperazinyl]-2-methyl-4-pyrimidinyl]amino]-5-thiazolecarboxamide depends on the type of formulation and the desired dosage regimen during administration time periods. The amount in each oral formulation may be from 0.1 to 200 mg, preferably from 20 to 100 mg.

Oral formulations may be solid formulations such as capsules, tablets, pills and troches, or a liquid suspension formulation.

The crystalline composition according to the invention may be used directly as powders (micronized particles), granules, suspensions, or they may be combined together with other pharmaceutically acceptable ingredients in admixing the components and optionally finely divide them, and then filling capsules, composed for example from hard or soft gelatin, compressing tablets, pills or troches, or suspend in suspensions. Coatings may be applied after compression to form pills.

Pharmaceutically acceptable ingredients are well known for the various types of formulation and may be for example binders such as natural or synthetic polymers, excipients, disintegrants, lubricants, surfactants, sweetening and other flavouring agents, coating materials, preservatives, dyes, thickeners, adjuvants, antimicrobial agents and carriers for the various formulation types.

Examples for binders are gum tragacanth, *acacia*, starch, gelatin, and biological degradable polymers such as homo- or co-polyesters of dicarboxylic acids, alkylene glycols, poly-alkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidone, und natural polymers like chitosan, carrageenan or hyaluronic acid.

Examples for excipients are phosphates such as dicalcium phosphate.

Examples for disintegrants are croscarmellose sodium, crospovidone, low-substituted hydroxypropyl cellulose, sodium starch glycolate or alginic acid.

Surfactants may be anionic, cationic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartame.

Examples for flavouring agents are peppermint, oil of wintergreen or fruit flavours like cherry or orange flavour.

Examples for coating materials are gelatin, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for solid carriers are talc, clay, microcrystalline cellulose, silica, alumina and the like.

The formulation according to the invention may also contain isotonic agents, such as sugars, buffers or sodium chloride.

The multicomponent crystalline system of the present invention may also be formulated as effervescent tablet or powder, which can disintegrate in an aqueous environment to provide a drinking solution.

The most preferred route is oral administration. The dosages may be conveniently presented in a unit dosage form and prepared by any of the methods well-known in the art of pharmacy.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The multicomponent crystalline system of the present invention and its formulations, respectively, can be also be administered in combination with other therapeutic agents being effective to treat a given condition and/or to provide a combination therapy. Preferably, the multicomponent crystalline system of the present invention further comprises Imatinib as active ingredient.

The multicomponent crystalline system of the present invention and the pharmaceutical composition according to the invention are useful for effective treatment of disorders in connection with need of inhibiting the BCR/ABL and Src family tyrosine kinases. The multicomponent crystalline system of the present invention and the respective pharmaceutical compositions are useful in the treatment of chronic myelogenous leukemia but also advanced prostate cancer.

The multicomponent crystalline system of the present invention and the pharmaceutical compositions according to the invention can also be used in a therapeutic method for producing an Abl tyrosine kinase inhibiting effect in a mammal comprising administering to a mammal in need of such therapy.

The multicomponent crystalline system of the present invention of the invention may be used as single component or as mixtures with other solid forms, which may be crystalline or amorphous.

Wherever noted, room temperature depicts a temperature from the range 18-23° C.; percentages are given by weight, if not indicated otherwise.

ABBREVIATIONS

DMSO dimethyl sulfoxide
HPLC high pressure liquid chromatography
NMR nuclear magnetic resonance
TG-FTIR thermogravimetry coupled with Fourier-transformation infrared spectrometry
r.h. relative humidity (air, if not indicated otherwise)
TGA thermogravimetry
v/v volume by volume
PXRD powder X-ray diffraction
Instrumental
Powder X-Ray Diffraction:

The measurements were carried out with a Bruker D8 Advance powder X-ray diffractometer using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The samples were prepared without any special treatment other than the application of slight pressure to get a flat surface. Generally, silicon single crystal sample holders of 0.1 mm depth were used. The tube voltage and current were 40 kV and 40 mA, respectively. The X-ray diffractometer is equipped with a LynxEye detector. A variable divergence slight was used with a 3° window. The step size was 0.02° 2θ with a step time of 37 seconds. The samples were rotated at 0.5 rps during the measurement.

Thermogravimetry Coupled to Infrared Spectroscopy (TG-FTIR):

Thermogravimetry coupled with FT-infrared spectroscopy is a well known method that allows to monitor the mass loss of a given sample upon heating while identifying the volatile substances by infrared spectroscopy. Therefore, TG-FTIR is a suitable method to identify solvates or hydrates.

TG-FTIR was performed on a Netzsch Thermo-Microbalance TG 209, which is coupled to a Bruker FT-IR Spectrometer Vector 22 or IFS 28. The measurements were carried out with aluminum crucibles with a micro pinhole under a nitrogen atmosphere and at a heating rate of 10° C./min over the range 25-250° C.

$^1$H-NMR:

The $^1$H-NMR spectra were recorded on a Bruker DPX 300 spectrometer. Solvent: Deuterated-DMSO Solubility Determinations:

Solubility determinations were carried out in pure water at 25±2° C. Suspensions with about 10 mg co-crystal in 0.5 mL water were prepared an equilibrated for two hours before the solution phase was filtered off and tested by HPLC.

HPLC:

HPLC was carried out on an Agilent 1100 HPLC chromatograph equipped with a UV-vis detection unit. The method is described by Mhaske, D. V. and Dhaneshwar, S. R. in Chromatographia 2007, 66(1/2), 95-102. The column type used was a Waters XTerra MS C18, 250×4.6 mm, 5 μm (FK-CC14). The method as referenced above is an isocratic method using an aqueous ammonium acetate/acetic acid and methanol with a ratio of 55/45. The applied flow rate was 1.0 mL per minute, the injection volume was 20 microliter and the detection wavelength was 321 nm.

Solvents: For all experiments, standard grade solvents are used.

The following examples illustrate the invention.

EXAMPLES

Example 1

Preparation of the Co-Crystal with methyl-4-hydroxybenzoate (Molar Ratio 3:1)

127.0 mg of dasatinib (monohydrate form) and 12.8 mg of methyl-4-hydroxybenzoate (Sigma-Aldrich No. 54750) are dissolved in 10 mL of methanol at 60° C. and stirred for 0.5 hour at 60° C. The solvent is evaporated using a dry nitrogen flow at 60° C. within approximately 1.5 hours and the dried sample is held at 60° C. for 1 hour. The sample is cooled and stored overnight at room temperature. Yield: approximately 112 mg. H-NMR spectroscopy indicates a molar ratio of dasatinib to methyl-4-hydroxybenzoate of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is an anhydrous, non-solvated solid form showing a PXRD pattern as in FIG. 1 with peak locations as indicated in table 2.

TABLE 2

D-spacing values for Dasatinib - methyl-4-hydroxybenzoate co-crystal (P013)

| 2θ Angle | d-spacing Å | Qualitative Intensity |
| --- | --- | --- |
| 6.0 | 14.7 | s |
| 6.9 | 12.8 | vs |
| 12.0 | 7.4 | vs |
| 12.4 | 7.1 | vs |
| 13.2 | 6.7 | s |
| 13.8 | 6.4 | s |
| 14.8 | 5.99 | w |
| 15.3 | 5.79 | m |
| 16.8 | 5.28 | s |
| 17.2 | 5.14 | m |
| 18.0 | 4.93 | w |
| 18.6 | 4.77 | w |
| 19.9 | 4.47 | w |
| 21.0 | 4.22 | s |
| 21.8 | 4.06 | m |
| 22.6 | 3.92 | w |
| 23.2 | 3.83 | w |
| 24.3 | 3.66 | vs |
| 24.8 | 3.58 | s |
| 26.0 | 3.42 | w |
| 26.7 | 3.33 | s |
| 27.9 | 3.20 | w | vs = very strong,
s = strong,
m = medium,
w = weak

Example 2

Preparation of the Co-Crystal with Nicotinamide (Molar Ratio 3:1)

127.2 mg of dasatinib (monohydrate form) and 10.1 mg of nicotinamide (Fluka No. 72345) are dissolved in 10 mL of methanol at 60° C. and stirred for 0.25 hour at 60° C. The solvent is evaporated using a dry nitrogen flow at 60° C. within approximately 2 hours and the dried sample is held at 60° C. for 1 hour. The sample is cooled and stored overnight at room temperature. Yield: approximately 107 mg. H-NMR spectroscopy indicates a molar ratio of dasatinib to nicotinamide of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 2 with peak locations as indicated in table 3.

TABLE 3

D-spacing values for Dasatinib - nicotinamide co-crystal (P026)

| 2θ Angle | d-spacing Å | Qualitative Intensity |
| --- | --- | --- |
| 5.4 | 16.4 | m |
| 5.9 | 14.9 | vs |
| 6.9 | 12.8 | vs |
| 10.7 | 8.2 | w |
| 11.5 | 7.7 | w |
| 11.8 | 7.5 | s |
| 12.4 | 7.1 | s |
| 13.2 | 6.7 | s |
| 13.8 | 6.4 | s |
| 15.1 | 5.88 | m |
| 15.9 | 5.56 | w |
| 16.8 | 5.28 | s |
| 17.7 | 5.02 | w |

TABLE 3-continued

D-spacing values for Dasatinib - nicotinamide co-crystal (P026)

| 2θ Angle | d-spacing Å | Qualitative Intensity |
|---|---|---|
| 18.6 | 4.78 | w |
| 19.3 | 4.60 | w |
| 21.2 | 4.19 | m |
| 21.8 | 4.07 | w |
| 22.1 | 4.02 | w |
| 24.4 | 3.64 | s |
| 24.9 | 3.57 | m |
| 25.4 | 3.50 | w |
| 26.1 | 3.41 | w |
| 27.8 | 3.20 | w |

Example 3

Preparation of the Co-Crystal with Ethyl Gallate (Molar Ratio 3:1)

127.3 mg of dasatinib (monohydrate form) and 16.7 mg of ethyl gallate (Aldrich No. 48640) are dissolved in 10 mL of methanol at 60° C. and stirred for 0.5 hour at 60° C. The solvent is evaporated using a dry nitrogen flow at 60° C. within approximately 1.5 hours and the dried sample is held at 60° C. for 1 hour. The sample is cooled and stored overnight at room temperature. Yield: approximately 124 mg. H-NMR spectroscopy indicates a molar ratio of dasatinib to ethyl gallate of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 3 with peak locations as indicated in table 4.

TABLE 4

D-spacing values for Dasatinib - ethyl galllate co-crystal (P169)

| 2θ Angle | d-spacing Å | Qualitative Intensity |
|---|---|---|
| 5.9 | 14.9 | m |
| 6.9 | 12.9 | vs |
| 11.1 | 8.0 | vw |
| 12.0 | 7.4 | m |
| 12.4 | 7.2 | vs |
| 13.2 | 6.7 | vs |
| 13.8 | 6.4 | s |
| 15.2 | 5.81 | w |
| 15.6 | 5.66 | w |
| 16.7 | 5.29 | vs |
| 17.2 | 5.15 | m |
| 17.8 | 4.98 | w |
| 18.5 | 4.78 | w |
| 19.3 | 4.60 | w |
| 20.3 | 4.38 | w |
| 21.1 | 4.21 | s |
| 21.8 | 4.07 | m |
| 22.1 | 4.02 | m |
| 23.2 | 3.83 | vw |
| 24.4 | 3.65 | vs |
| 24.9 | 3.58 | s |
| 26.0 | 3.42 | w |
| 27.8 | 3.20 | m |

Example 4

Preparation of the Co-Crystal with Ethyl Maltol (Molar Ratio 4:1)

126.9 mg of dasatinib (monohydrate form) and 12.4 mg of ethyl maltol (SAFC No. W348708) are dissolved in 10 mL of methanol at 60° C. and stirred for 0.5 hour at 60° C. The solvent is evaporated using a dry nitrogen flow at 60° C. within approximately 1.5 hours and the dried sample is held at 60° C. for 1 hour. The sample is cooled and stored overnight at room temperature. Yield: approximately 119 mg. H-NMR spectroscopy indicates a molar ratio of dasatinib to ethyl maltol of 4:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 4 with peak locations as indicated in table 5.

TABLE 5

D-spacing values for Dasatinib - ethylmaltol co-crystal (P171)

| 2θ Angle | d-spacing Å | Qualitative Intensity |
|---|---|---|
| 5.9 | 15.0 | vs |
| 6.9 | 12.8 | vs |
| 11.8 | 7.5 | s |
| 12.4 | 7.1 | s |
| 13.2 | 6.7 | s |
| 13.8 | 6.4 | s |
| 14.9 | 5.93 | m |
| 16.8 | 5.28 | s |
| 17.3 | 5.12 | w |
| 18.6 | 4.76 | vw |
| 19.3 | 4.60 | w |
| 20.3 | 4.37 | vw |
| 21.0 | 4.23 | W |
| 21.5 | 4.12 | w |
| 23.0 | 3.86 | w |
| 24.3 | 3.66 | m |
| 24.9 | 3.58 | m |
| 25.5 | 3.49 | w |
| 26.0 | 3.42 | vw |
| 27.9 | 3.19 | w |

Example 5

Preparation of the Co-Crystal with Vanillin (Molar Ratio 3:1)

126.9 mg of dasatinib (monohydrate form) and 13.0 mg of vanillin (Fluka No. 94752) are dissolved in 10 mL of methanol at 60° C. and stirred for 1 hour at 60° C. The solvent is evaporated using a dry nitrogen flow at 60° C. within approximately 2.5 hours and the dried sample is held at 60° C. for 1 hour. The sample is cooled and stored overnight at room temperature. Yield: approximately 120 mg. H-NMR spectroscopy indicates a molar ratio of dasatinib to vanillin of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 5 with peak locations as indicated in table 6.

TABLE 6

D-spacing values for Dasatinib - vanillin co-crystal (P173)

| 2θ Angle | d-spacing Å | Qualitative Intensity |
|---|---|---|
| 5.9 | 15.0 | m |
| 6.9 | 12.8 | vs |
| 11.2 | 7.9 | w |
| 12.4 | 7.1 | vs |
| 13.2 | 6.7 | vs |
| 13.8 | 6.4 | s |
| 15.6 | 5.66 | w |
| 16.0 | 5.52 | w |
| 16.7 | 5.29 | s |
| 17.2 | 5.14 | m |
| 17.7 | 5.01 | w |
| 17.9 | 4.94 | w |
| 18.6 | 4.77 | w |
| 19.3 | 4.59 | w |
| 19.9 | 4.46 | vw |
| 20.3 | 4.38 | w |
| 21.1 | 4.21 | s |
| 21.9 | 4.06 | m |
| 22.5 | 3.95 | w |
| 23.2 | 3.83 | w |
| 24.1 | 3.69 | s |
| 24.4 | 3.65 | s |
| 24.9 | 3.57 | s |
| 25.4 | 3.50 | w |
| 26.3 | 3.38 | w |
| 27.9 | 3.20 | w |
| 28.4 | 3.14 | vw |

Example 6

Preparation of the Co-Crystal with Methyl Gallate (Molar Ratio 3:1)

127.3 mg of dasatinib (monohydrate form) and 15.5 mg of methyl gallate (Aldrich No. 274194) are dissolved in 10 mL of methanol at 60° C. and stirred for 0.5 hour at 60° C. The solvent is evaporated using a dry nitrogen flow at 60° C. within approximately 1.5 hours and the dried sample is held at 60° C. for 1 hour. The sample is cooled and stored overnight at room temperature. Yield: approximately 123 mg. H-NMR spectroscopy indicates a molar ratio of dasatinib to methyl gallate of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 6 with peak locations as indicated in table 7.

TABLE 4

D-spacing values for Dasatinib - methyl gallate co-crystal (P288)

| 2θ Angle | d-spacing Å | Qualitative Intensity |
|---|---|---|
| 6.0 | 14.8 | vs |
| 6.8 | 12.9 | vs |
| 12.0 | 7.4 | s |
| 12.3 | 7.2 | s |
| 13.1 | 6.7 | s |
| 13.7 | 6.5 | s |
| 15.0 | 5.90 | w |
| 15.5 | 5.71 | s |
| 16.4 | 5.41 | vw |
| 16.7 | 5.30 | m |
| 17.2 | 5.16 | w |
| 18.0 | 4.92 | m |
| 18.4 | 4.83 | vw |

TABLE 4-continued

D-spacing values for Dasatinib - methyl gallate co-crystal (P288)

| 2θ Angle | d-spacing Å | Qualitative Intensity |
|---|---|---|
| 18.7 | 4.74 | w |
| 19.2 | 4.62 | vw |
| 20.2 | 4.40 | vw |
| 21.1 | 4.21 | w |
| 21.8 | 4.07 | m |
| 23.5 | 3.79 | w |
| 24.3 | 3.67 | m |
| 24.9 | 3.58 | s |
| 26.2 | 3.40 | w |
| 27.8 | 3.21 | w |

Example 7

Preparation of the Co-Crystal with (1R,2S,5R)-(−)-menthol (Molar Ratio 3:1)

127.0 mg of dasatinib (monohydrate form) and 19.7 mg of (1R,2S,5R)-(−)-menthol (Sigma-Aldrich No. M278-0) are dissolved in 10 mL of methanol at 60° C. and stirred for 0.5 hour at 60° C. The solvent is evaporated using a dry nitrogen flow at 60° C. within approximately two hours and the dried sample is held at 60° C. for 1 hour. The sample is cooled and stored overnight at room temperature. Yield: approximately 120 mg. H-NMR spectroscopy indicates a molar ratio of Dasatinib to menthol of 3:1. The solid material is further characterized by PXRD and TG-FTIR. Thermogravimetry coupled with FT infrared spectroscopy shows that the obtained material is neither a solvate, nor a hydrate. This result shows that the obtained co-crystal is a non-solvated solid form showing a PXRD pattern as in FIG. 7 with peak locations as indicated in table 8.

TABLE 8

D-spacing values for dasatinib - (1R,2S,5R,)-(—)-menthol co-crystal (P292)

| 2θ Angle | d-spacing Å | Qualitative Intensity |
|---|---|---|
| 5.8 | 15.2 | vs |
| 6.8 | 13.0 | s |
| 10.4 | 8.5 | vw |
| 11.7 | 7.5 | s |
| 12.3 | 7.2 | w |
| 12.7 | 7.0 | vw |
| 13.1 | 6.8 | w |
| 13.7 | 6.5 | m |
| 14.7 | 6.03 | vw |
| 14.9 | 5.92 | s |
| 15.7 | 5.65 | w |
| 16.1 | 5.51 | vw |
| 16.5 | 5.38 | vw |
| 16.7 | 5.32 | vw |
| 17.2 | 5.16 | vw |
| 17.6 | 5.03 | w |
| 18.2 | 4.87 | w |
| 18.4 | 4.83 | vw |
| 18.7 | 4.75 | vw |
| 19.2 | 4.63 | vw |
| 21.1 | 4.21 | w |
| 21.3 | 4.17 | m |
| 21.8 | 4.08 | w |
| 22.0 | 4.03 | vw |
| 22.8 | 3.90 | w |
| 23.9 | 3.72 | m |
| 24.4 | 3.64 | w |
| 24.8 | 3.58 | w |
| 25.9 | 3.44 | vw |

TABLE 8-continued

D-spacing values for dasatinib - (1R,2S,5R,)-(—)-menthol co-crystal (P292)

| 2θ Angle | d-spacing Å | Qualitative Intensity |
|---|---|---|
| 27.3 | 3.26 | w |
| 28.0 | 3.19 | w |
| 29.7 | 3.01 | vw |

Figure 1:
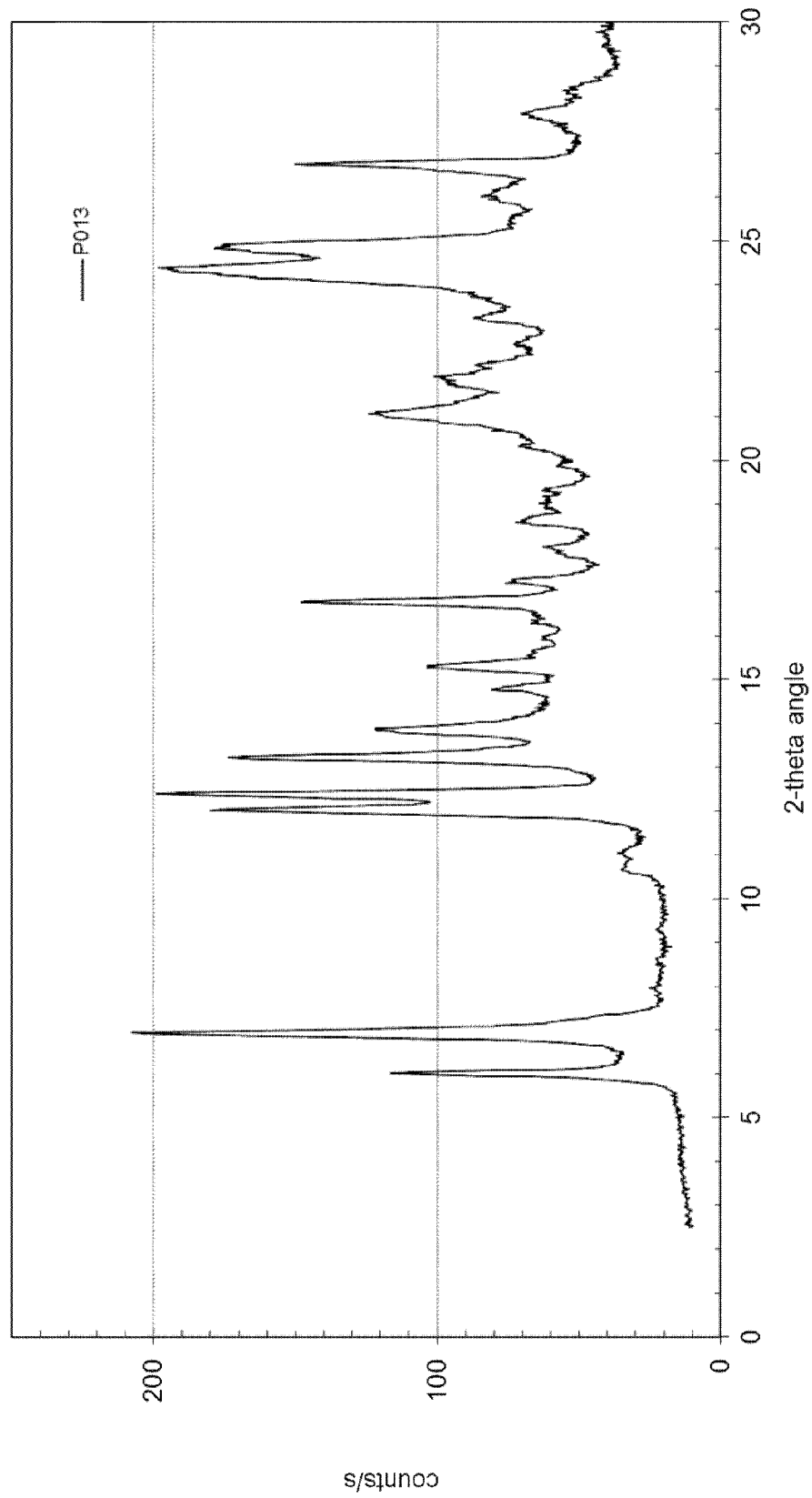
FIG. 1: Powder X-ray diffraction pattern of the dasatinib-methyl-4-hydroxybenzoate co-crystal.
Figure 2:
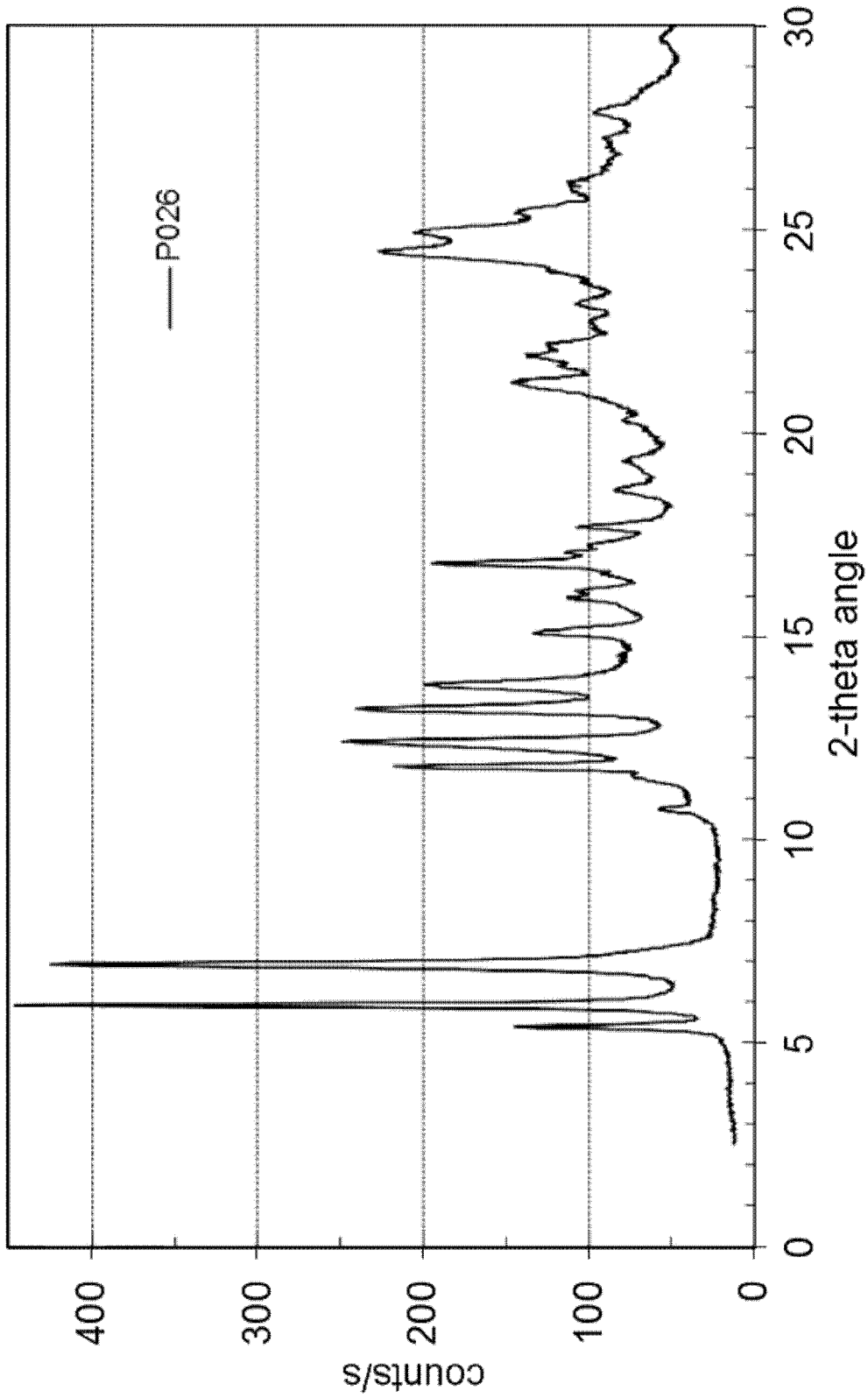
FIG. 2: Powder X-ray diffraction pattern of the dasatinib-nicotinamide co-crystal.
Figure 3:
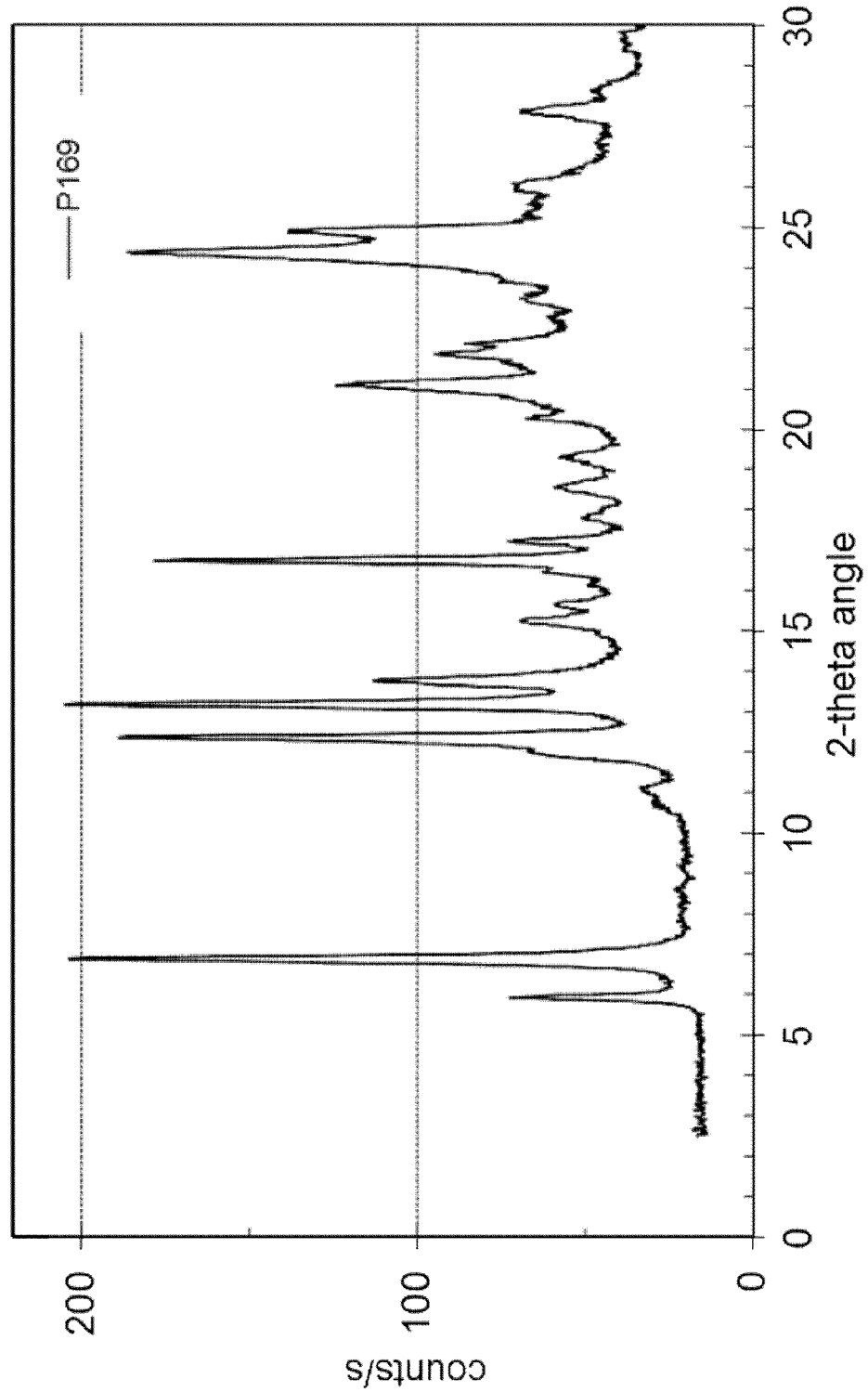
FIG. 3: Powder X-ray diffraction pattern of the dasatinib-ethyl gallate co-crystal.
Figure 4:
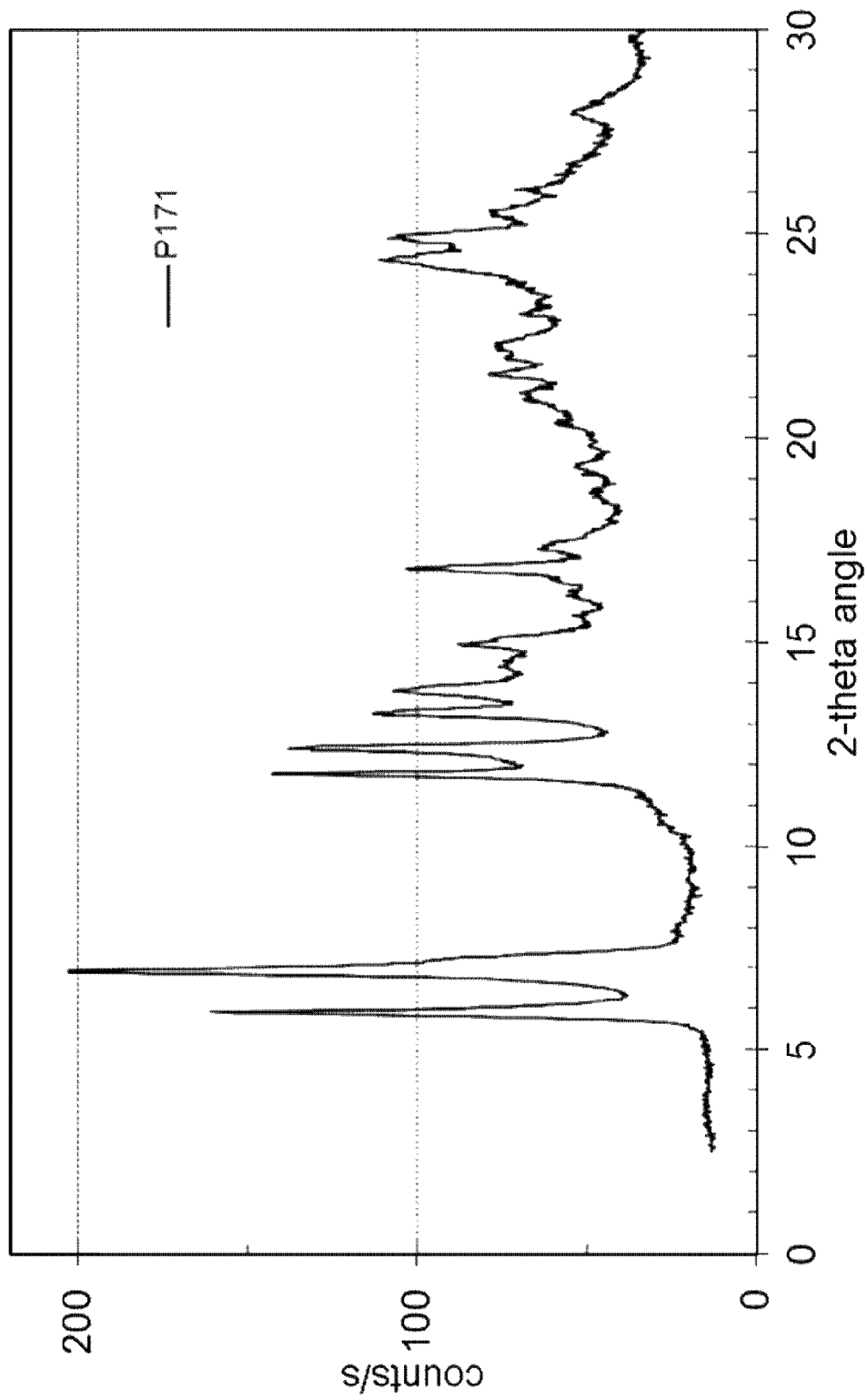
FIG. 4: Powder X-ray diffraction pattern of the dasatinib-ethyl maltol co-crystal.
Figure 5:
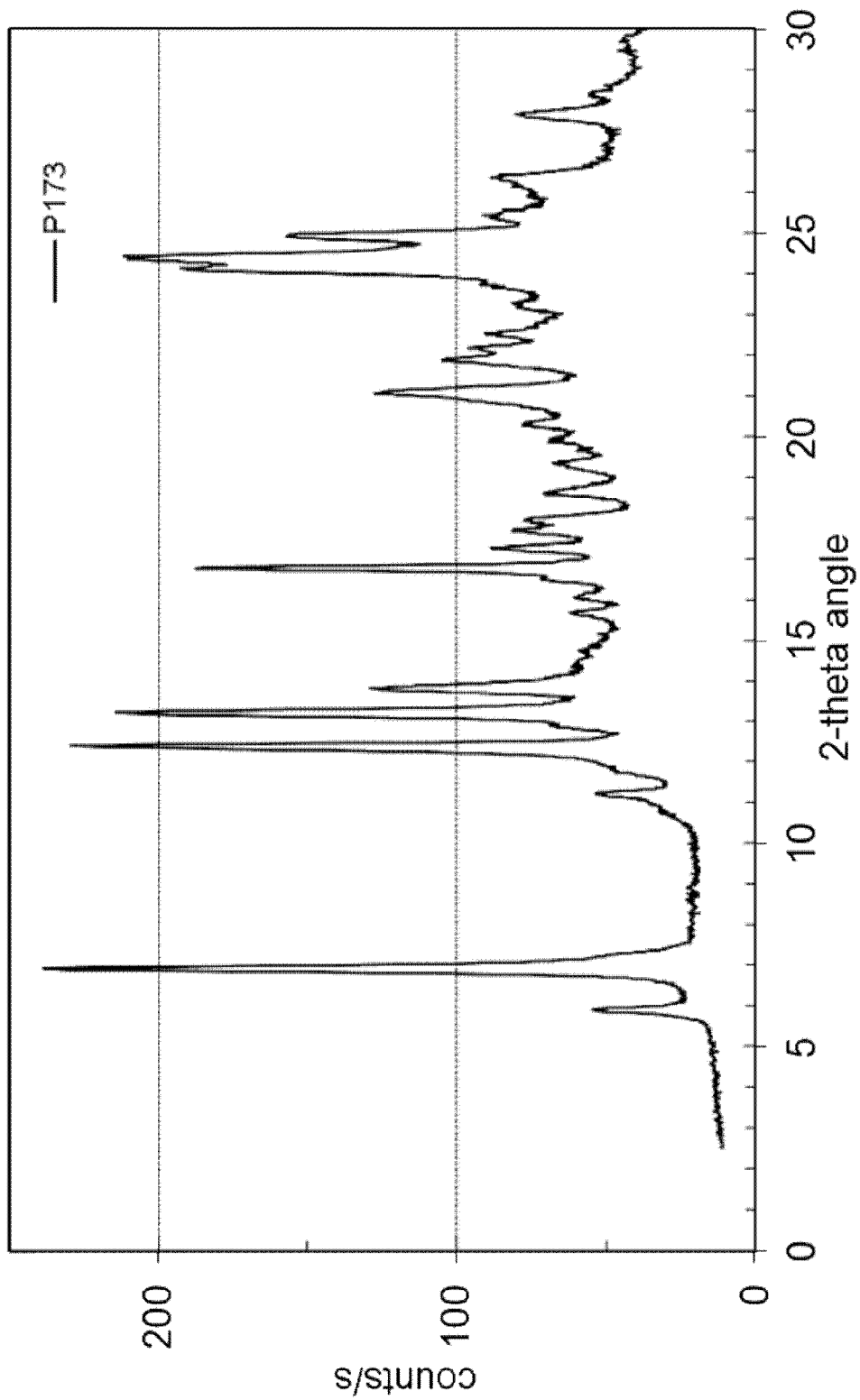
FIG. 5: Powder X-ray diffraction pattern of the dasatinib-vanillin co-crystal.
Figure 6:
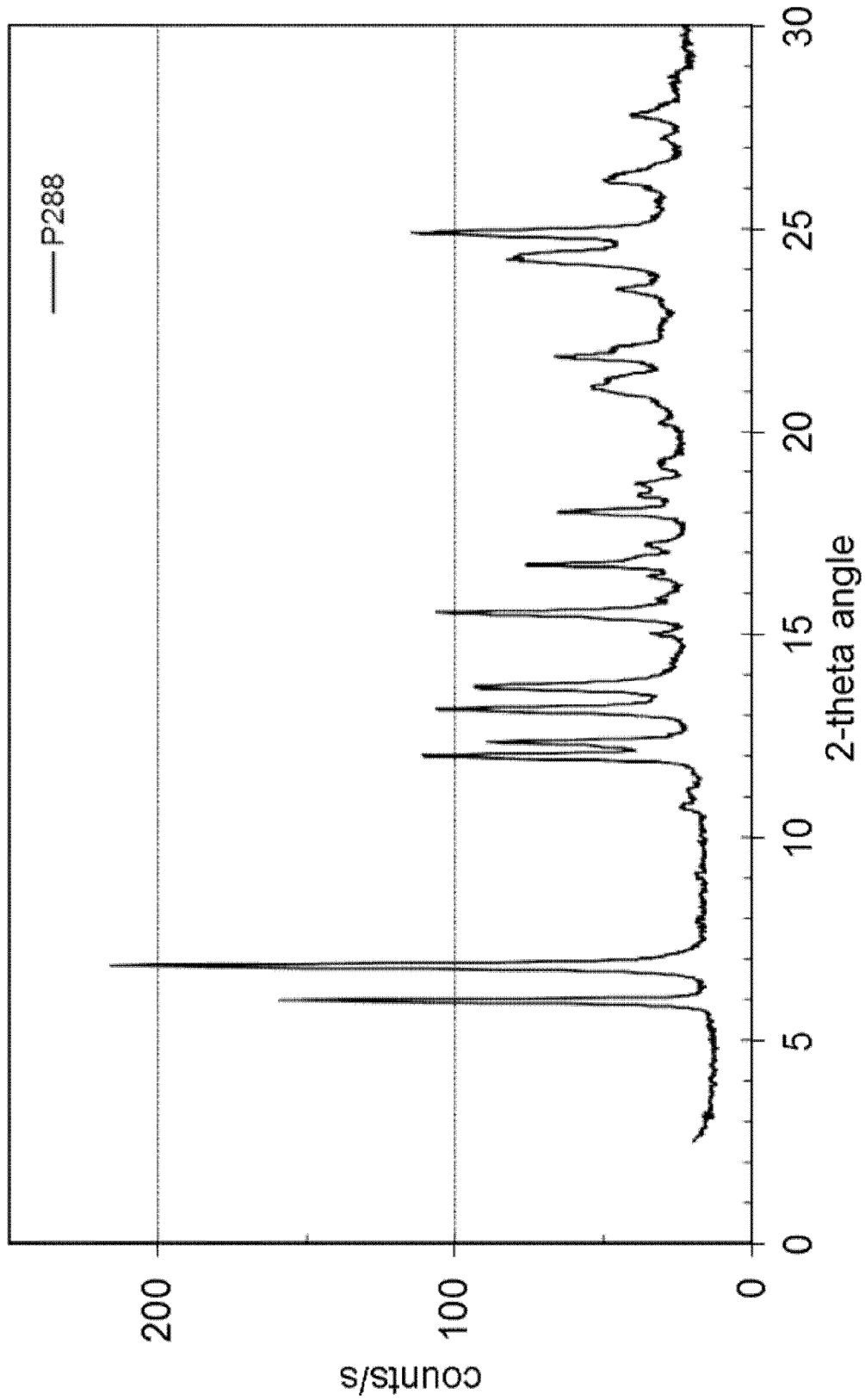
FIG. 6: Powder X-ray diffraction pattern of the dasatinib-methyl gallate co-crystal.
Figure 7:
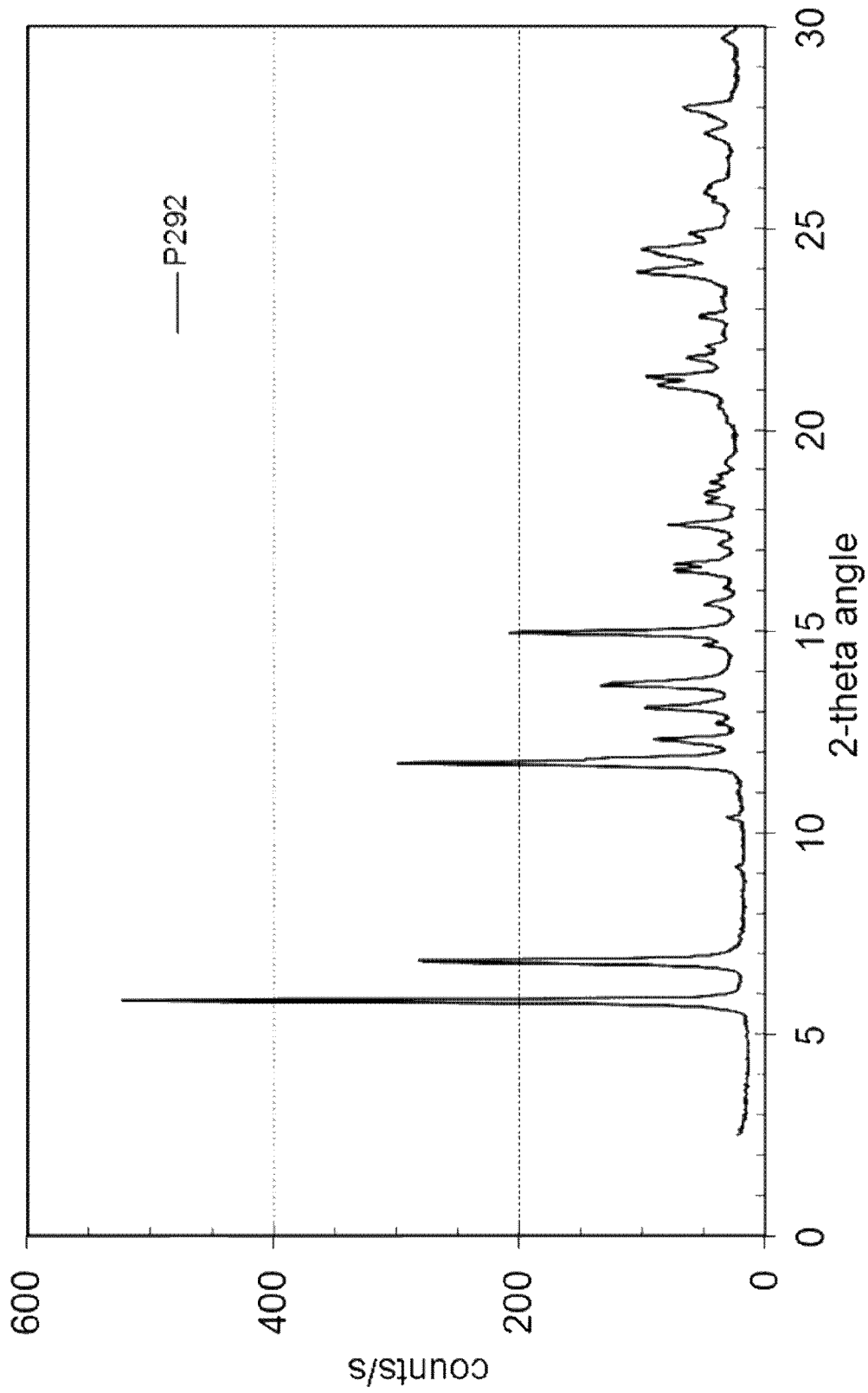
FIG. 7: Powder X-ray diffraction pattern of the dasatinib-(1R,2S,5R)-(−)-menthol co-crystal.

The invention claimed is:

1. A multicomponent crystalline system, comprising:
a compound of formula 1

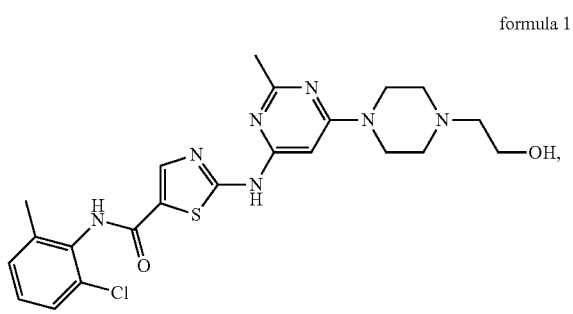 [SMILES: Cc1nc(Nc2ncc(C(=O)Nc3c(C)cccc3Cl)s2)cc(N2CCN(CCO)CC2)n1]

formula 1 and
a second compound selected from the group consisting of methyl-4-hydroxybenzoate, nicotinamide, ethyl gallate, methyl gallate, propyl gallate, ethyl maltol, vanillin, menthol, and (1R,2S,5R)-(−)-menthol.

2. The multicomponent crystalline system according to claim 1, wherein a molar ratio of the compound of formula 1 to the second compound is from 7:1 to 1:1.

3. The multicomponent crystalline system according to claim 1, wherein the second compound is methyl-4-hydroxybenzoate and has a PXRD pattern with at least one characteristic peak expressed in 2θ±0.2° 2θ measured using CuKα radiation at 6.0, 6.9, 12.0, 12.4, 13.2, and 24.3°.

4. The multicomponent crystalline system according to claim 1, wherein the second compound is nicotinamide and has a PXRD pattern with at least one characteristic peak expressed in 2θ±0.2° 2θ measured using CuKα radiation at 5.4, 5.9, 6.9, 12.4, 13.2, and 24.4°.

5. The multicomponent crystalline system according to claim 1, wherein the second compound is ethyl gallate and has a PXRD pattern with at least one characteristic peak expressed in 2θ±0.2° 2θ measured using CuKα radiation at 5.9, 6.9, 12.4, 13.2, 16.7, 21.1, and 24.4°.

6. The multicomponent crystalline system according to claim 1, wherein the second compound is ethyl maltol and has a PXRD pattern with at least one characteristic peak expressed in 2θ±0.2° 2θ measured using CuKα radiation at 5.9, 6.9, 11.8, 12.4, 13.2, and 16.8°.

7. The multicomponent crystalline system according to claim 1, wherein the second compound is vanillin and has a PXRD pattern with at least one characteristic peak expressed in 2θ±0.2° 2θ measured using CuKα radiation at 5.9, 6.9, 12.4, 13.2, 16.7, and 24.4°.

8. The multicomponent crystalline system according to claim 1, wherein the second compound is methyl gallate and has a PXRD pattern with at least one characteristic peak expressed in 2θ±0.2° 2θ measured using CuKα radiation at 6.0, 6.8, 12.0, 13.1, 15.5, and 24.9°.

9. The multicomponent crystalline system according to claim 1, wherein the second compound is (1R,2S,5R)-(−)-menthol.

10. The multicomponent crystalline system according to claim 1, wherein the second compound is (1R,2S,5R)-(−)-menthol and has a PXRD pattern with at least one characteristic peak expressed in 2θ±0.2° 2θ measured using CuKα radiation at 5.8, 6.8, 11.7, 13.7, and 14.9°.

11. A method for treating chronic myelogenous leukemia, the method comprising: administering the multicomponent crystalline system according to claim 1 to a recipient in need thereof.

12. A process for obtaining the multicomponent crystalline system according to claim 1, the process comprising:
a) adding the second compound to a mixture of the compound of formula 1 and a suitable solvent or solvents, thereby obtaining a composition;
b) optionally concentrating the composition;
c) crystallizing the composition, thereby obtaining a suspension;
d) optionally evaporating to dryness or equilibrating the suspension, thereby obtaining a precipitate; and
e) isolating the precipitate, thereby obtaining the multicomponent crystalline system.

13. The process according to claim 12, wherein a molar ratio of the compound of formula 1 to the second compound is from 7:1 to 1:1.

14. The process according claim 12, wherein the second compound is in solid form, or as a solution an alcohol, a ketone, an acetate, of a mixture of solvents optionally comprising water.

15. The process according to claim 12, wherein the second compound is (1R,2S,5R)-(−)-menthol.

16. The process according to claim 12, wherein the solvent is a water miscible organic solvent.

17. The process according to claim 12, wherein seed crystals are added in c) and/or d).

18. A pharmaceutical composition, comprising:
the multicomponent crystalline system according to claim 1, and
optionally one or more pharmaceutically acceptable excipients.

19. The pharmaceutical composition according to claim 18, further comprising: Imatinib as an active ingredient.

* * * * *